United States Patent [19]
Cardin et al.

[11] Patent Number: 5,104,645
[45] Date of Patent: Apr. 14, 1992

[54] ANTIDANDRUFF SHAMPOO COMPOSITIONS

[75] Inventors: Caroline W. Cardin; Joyce I. Davis; Judi L. Hart; Diane G. Schmidt

[73] Assignee: The Proctor & Gamble Company, Cincinnati, Ohio

[21] Appl. No.: 472,041

[22] Filed: Feb. 2, 1990

[51] Int. Cl.$^5$ ................................................ A61K 7/75
[52] U.S. Cl. ........................... 424/70; 424/DIG. 4; 252/DIG. 13; 252/106; 252/174.21; 252/174.22; 252/174.17; 252/174.15; 514/852
[58] Field of Search ............ 424/70, DIG. 4, 78; 252/106, 174.15, 174.17, 174.21, 174.22, DIG. 13; 514/852

[56] References Cited

U.S. PATENT DOCUMENTS

| | | | |
|---|---|---|---|
| 2,809,971 | 10/1957 | Bernstein et al. | 546/6 |
| 3,236,733 | 2/1966 | Karsten et al. | 514/188 |
| 3,753,916 | 8/1973 | Parran | 252/107 |
| 3,761,417 | 9/1973 | Parran | 252/106 |
| 3,761,418 | 9/1973 | Parran | 252/106 |
| 4,166,845 | 9/1979 | Hansen | 424/70 |
| 4,185,106 | 2/1980 | Dittman | 424/DIG. 4 |
| 4,323,683 | 4/1982 | Bolich et al. | 546/6 |
| 4,345,080 | 8/1982 | Bolich Jr. | 546/6 |
| 4,379,753 | 4/1983 | Bolich | 252/106 |
| 4,405,645 | 9/1983 | Rothlisberger | 424/70 |
| 4,470,982 | 9/1984 | Winkler | 514/188 |
| 4,492,646 | 1/1985 | Welch | 252/174.21 |
| 4,557,928 | 12/1985 | Glover | 424/DIG. 4 |
| 4,559,227 | 12/1985 | Chandra | 424/DIG. 4 |
| 4,631,187 | 12/1986 | Padden | 424/70 |
| 4,711,775 | 12/1987 | Dittman | 424/DIG. 4 |
| 4,801,447 | 1/1989 | Gum | 424/70 |
| 4,898,725 | 2/1990 | Hoeffkes | 424/70 |
| 4,935,224 | 6/1990 | Rosso | 424/65 |

FOREIGN PATENT DOCUMENTS 285388 10/1988 European Pat. Off.
57-80644 11/1983 Japan.

OTHER PUBLICATIONS

Babar et al., In-Vitro Release Of Zinc Pyrethhione From A Shampoo Base And The Effect Of Various Additives On Its Release Rate, Drug Development and Industrial Pharmacy, 11(8), 1507-1522 (1985).

R. L. Goldemberg, Advances In Cosmetic Technology, vol. 1, pp. 70-71 (1978).

Primary Examiner—Thurman K. Page
Assistant Examiner—Susan S. Rucker
Attorney, Agent, or Firm—John M. Howell; Goldstein, Steven J.; Leonard W. Lewis

[57] ABSTRACT

Antidandruff shampoos comprising a surfactant, platelet zinc pyridinethione active of specific particle size, a suspending agent, water, and a synergizer for the active. Said compositions have superior efficacy when compared with antidandruff shampoos known in the art.

23 Claims, No Drawings

ANTIDANDRUFF SHAMPOO COMPOSITIONS

TECHNICAL FIELD

The present invention relates to antidandruff shampoos. These shampoos exhibit excellent antidandruff activity.

BACKGROUND OF THE INVENTION

Antidandruff shampoos are well known in the art and rely upon various actives for their antidandruff effectiveness. Such compositions are not only designed to relieve the dandruff condition, but also to effectively clean the hair.

U.S. Pat. No. 3,917,817, Vanlerberghe et al., issued Nov. 5, 1975, discloses a shampoo composition comprising a piperazine based cationic polymer active, 10% sodium alkyl sulfate, 4% lauryl monoethanolamide and 3% glycol distearate. U.S. Pat. No. 4,013,787, Vanlerberghe et al., issued Mar. 22, 1977, discloses similar compositions.

Pyridinethione slats are known for use as dandruff control actives. Specifically, 1-hydroxypyridinethione salts have been taught as antidandruff actives in lotion form shampoos. Included in this group is 2-zinc pyrithion (ZPT) as disclosed in U.S. Pat. No. 2,809,971, Bernstein, issued Oct. 15, 1957; U.S. Pat. No. 3,236,733, Karsten, issued Feb. 22, 1966; U.S. Pat. No. 3,753,916, Parran, issued Aug. 21, 1973; Japanese Published Application 60810, published May 19, 1977 (Lion Fat and Oil); U.S. Pat. No. 4,323,683, Bolich et al., issued Apr. 6, 1982; U.S. Pat. No. 4,345,080, Bolich, issued Aug. 17, 1982; U.S. Pat. No. 4,379,753, Bolich, issued Apr. 12, 1983; U.S. Pat. No. 4,470,982, Winkler, issued Sept. 11, 1984; and European Published Patent Application No. 285,388, published Oct. 5, 1988 abandoned.

In the present invention it has been surprisingly found that when a pyridinethione metal salt in platelet form, with a specified particle size, is combined with any of a group of specific synergizers in a shampoo matrix, an unexpected substantial improvement in antidandruff efficacy is realized. Such compositions are stable, safe and effective in cleaning the hair while treating the scalp for dandruff.

SUMMARY OF THE INVENTION

The present invention relates to shampoo compositions comprising:
(a) from about 5% to about 70% of a synthetic surfactant;
(b) from about 0.3% to about 2% of pyridinethione metal salt in platelet particle form having a mean particle size of from about 2 microns to about 15 microns;
(c) from about 0.5% to about 5% of a synergizer selected from the group consisting of polyethylene glycols containing from about 6 to about 22 ethylene oxide units, polypropylene glycols containing from about 6 to about 22 propylene oxide units, polyoxamer block polymers, polyethylene oxide fatty glycerides, polyethylenimines containing from about 6 to about 22 imine groups, polyethoxylated polyethylenimies, polyethylene oxide carbohydrates, ethoxylated nonylphenols, ethoxylated alcohols, and mixtures thereof (preferred synergizers include the polyethylene glycols, particularly PEG-12);
(d) from about 0.5% to about 6% of a suspending agent; and
(e) the remainder water.

These antidandruff shampoos are effective in cleansing the hair, as well as effectively treating dandruff. These compositions may also include additional antidandruff actives and/or silicone polymers to conditions the hair without interrupting the treatment of said dandruff. The lotion form is particularly preferred for the shampoos.

All ratios, percentages and parts given herein are "by weight" unless otherwise specified.

DETAILED DESCRIPTION OF THE INVENTION

The essential components of the present invention as well as optional components, are set forth in the following paragraphs.

SURFACTANT

An essential component of the present compositions is a synthetic surfactant. The surfactant, which may be selected from any of a wide variety of synthetic anionic, amphoteric, zwitterionic and nonionic surfactants typically used in shampoos, is present at a level of from about 5% to about 70%, preferably from about 10% to about 30%, most preferably from about 10% to about 22%, of the composition.

Synthetic anionic surfactants can be exemplified by the alkali metal salts or organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acids monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium slats of alkyl phenol ethylene oxide ether sulfate with 1 to 10 units of ethylene oxide per molecular and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water-solubilizing group, e.g., carboxy, sulfonate, sulfate, phosphate, or phosphonate. A general formula for these compounds is:

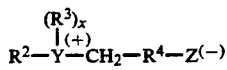

wherein $R^2$ contains an alkyl, alkenyl, or hydroxyalkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms, x is 1 when Y is a sulfur atom and 2 when Y is a nitrogen or phosphorus atom; $R^4$ is an alkylene or hydroxyalkylene of from 1 to about 4 carbon atoms; and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxypentane-1-sulfate.

Other zwitterionics, such as betaines, are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gammacarboxypropyl betaine, and lauryl bis-(2-hydroxypropyl) alphacarboxyethyl betaine. The sulfobetaines may be represented by, for example, coco dimethyl sulfopropyl betaine, stearyl dimethyl sulfopropyl betaine, lauryl dimethyl sulfoethyl betaine, and lauryl bis-(2-hydroxyethyl) sulfopropyl betaine. Amido betaines and amidosulfobetaines, wherein the $RCONH(CH_2)_3$ radical is attached to the nitrogen atom of the betaine, are also useful in this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxide corresponding to the following general formula:

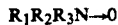

$$R_1R_2R_3N \rightarrow 0$$

wherein $R_1$ contains an alkyl, alkenyl or monohydroxyalkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyldecylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow 0$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety, and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl)phosphine oxide, stearyldimethylphosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dedecyldi(2-hydroxyethyl)phosphine oxide, tetradecylmethyl-2-hydroxypropylphosphine oxide oleyldimethylphosphine oxide, 2-hydroxydedecyldimethylphosphine oxide.

6. Long chain dialkyl sulfoxides containing one short chain alkyl or hydroxyalkyl radical of 1 to about 3 carbon atoms (usually methyl) and one long hydrophobic chain which contains alkyl, alkenyl, hydroxyalkyl, or keto alkyl radicals containing from about 8 to about 20 carbon atoms, from 0 to about 10 ethylene oxide moieties and from 0 to 1 glyceryl moiety. Examples include octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants, useful herein, are described in *McCutcheon's Detergents and Emulsifiers*, 1979 *Annual*, published by Allured Publishing Corporation, which is incorporated herein by reference.

The above-mentioned surfactants can be used alone or in combination in the shampoo compositions of the present invention. The anionic surfactants, particularly the alkyl sulfates, the ethoxylated alkyl sulfates and mixtures thereof, as well as the isethionates, are preferred for use herein. Most preferred are the mixtures of alkyl sulfate and ethoxylated alkyl sulfate, wherein the ratios of the former to the latter are from about 1:5 to about 5:1. Most preferred contains ammonium lauryl sulfate and ammonium laureth sulfate.

When these surfactants are introduced into the composition it is preferred they be introduced as mixtures having a surfactant concentration of about 28% in the case of ammonium laureth sulfate and about 25% in the case of ammonium lauryl sulfate. These concentrations allow for optimum processing of the shampoo compositions.

ANTIDANDRUFF ACTIVE

In the present invention, the antidandruff active is a 1-hydroxy-2-pyridinethione salt in platelet particle form, wherein the particles have an average size of from 2 microns to about 15 microns, preferably from about 5 microns to about 9 microns. The active is used at a level of from about 0.3% to about 2%, preferably about 1%, of the shampoo composition. The 1-hydroxy-2-pyridinethione salts are disclosed for use in antidandruff shampoos in U.S. Pat. No. 2,809,971, Bernstein, issued Oct. 15, 1957; U.S. Pat. No. 3,236,733, Karsten et al., issued Feb. 22, 1966; U.S. Pat. No. 3,753,196, Parran, issued Aug. 21, 1973; U.S. Pat. No. 3,761,418, Parran, issued Sept. 25, 1973; U.S. Pat. No. 4,345,080, Bolich, issued Aug. 17, 1982; U.S. Pat. No. 4,323,683, Bolich et al., issued Apr. 6, 1982; U.S. Pat. No. 4,379,753, Bolich issued Apr. 12, 1983; and U.S. Pat. No. 4,470,982, Winkler, issued Sept. 11, 1984; all incorporated herein by reference.

The pyridinethione salts useful herein can generally be defined as water-insoluble salts of 1-hydroxy-2-pyridinethione which has the following structural formula in tautomeric form, the sulfur being attached to the No. 2 position in the pyridine ring.

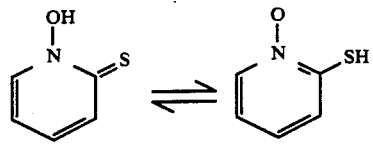

The salts result from substitution of the hydrogen of one of the tautomeric forms by the appropriate salt cation. Depending, of course, on the valence of the salt cation involved there may be more than one of the pyridinethione rings in the compound.

Preferred slats are formed from metals such as zinc, tin, cadmium, magnesium, aluminium and zirconium. The most preferred metal herein is zinc which forms 2-zinc pyrithione or ZPT. Other cations such as sodium are also suitable.

The pyridinethione salts useful herein take the form of water-insoluble flat platelet particles which have a mean sphericity of less than about 0.65, preferably from about 0.20 to about 0.54, and a median particle size of from about 2 $\mu$ to about 15 $\mu$, preferably from about 5 $\mu$ to about 9 $\mu$, the particle size being expressed as the median equivalent diameter of a sphere of equal volume. The median diameters are on a mass basis with 50% of the mass of particles falling on either side of the value given.

The diameter of a sphere of equivalent volume for a particle can be determined by a variety of sedimentation techniques which are based on Stokes' Law for the settling velocity of a particle in a fluid. Such techniques are described in Stockham, J. D. and Fochtam, E. G., *Particles Size Analysis*, Ann Arbor Science, 1978, incorporated herein by reference. An approach for determining the median equivalent spherical diameter based on volume, $d_v$, is shown in U.S. Pat. No. 4,345,080, Bolich, issued Aug. 17, 1982, Example II, incorporated herein by reference.

The sphericity of a particle is also described by Stockham and Fochtman, supra, at page 113, as $(d_v/d_S)^2$, where $d_v$ is the diameter of a sphere of equivalent volume, supra, and $d_s$ is the diameter of a sphere of equivalent area. As used herein, however, the mean sphericity is $(d_v/d_s)^2$ or the surface are of spheres having equivalent volume distribution divided by the actual surface area of particles as measured. A technique for determining actual surface area is shown in the examples using the BET technique described by Stockham and Fochtam, supra, at page 122.

From the viewpoint of antidandruff efficacy, the BET surface area herein preferably falls in the range of from about 0.5 to about 3.5 $m^2/g$, more preferably from about 1.0 to about 3.0 $m^2/g$.

The platelet 2-zinc pyrithione crystals preferred herein are made in the manner disclosed in U.S. Pat. No. 4,323,683, Bolich et al., issued Apr. 6, 1982; U.S. Pat. No. 4,345,080, Bolich, issued Aug. 17, 1982; and U.S. Pat. No. 4,379,753, Bolich, issued Apr. 12, 1983; all of which are incorporated herein by reference.

In addition to the 1-hydroxy-2-pyridinethione salts, the shampoo composition disclosed herein may include other known antidandruff actives. Such antidandruff actives, when used, are included at levels of from about 0.1% to about 1% of the composition, and are selected from the group consisting of hydroxypyridone salts, selenium disulfide, and mixtures thereof.

Hydroxypyridone salts are known antimicrobials. See *Cosmetics and Drug Preservation, Principles and Practice*, p 742 (edited by J. Kabura, 1984), incorporated herein by reference. The hydroxypyridone salts used herein can generally be described as 1-hydroxy-4-methyl-(1H)-pyridones having an aliphatic or aromatic moiety (R) at the 6 position thereof, wherein R has a $\pi$ factor of at least 1:3, preferably from 2 to 6, more preferably from 3 to 5.5. The $\pi$ factor is a measure of the lipophilicity/hydrophilicity of the substituent and is defined in detail in the paper by W. Dittmar, E. Druckrey and H. Urbach, J. Med. Chem. 17(7), 753-6(1974) and references cited therein; all of which are incorporated herein by reference.

In structural terms, preferred R substituents are selected from linear and branched $C_3$-$C_{11}$, preferably $C_6$-$C_{11}$, alkyl and alkenyl groups, $C_5$-$C_8$ cycloalkyl groups, and $C_5$-$C_8$ aryl groups. The cyclic moieties, discussed above, can also be substituted with one or more alkyl or alkenyl groups up to $C_4$. The R groups can further be substituted with halogen atoms. Of the above, preferred R moieties are cyclohexyl and 2,4,4-trimethyl pentyl, the latter being highly preferred.

The above mentioned compounds can be used both in the free form and as salts, for example, salts with organic bases or inorganic cations. Low molecular weight alkanolamines are especially preferred organic bases. The preferred hydroxypyridone salt for use herein is the monoethanolamine slat known as piroctone olamine or Octopirox; see *Cosmetic and Drug Preservation*, supra.

Piroctone olamine is described for use in deodorant compositions in Japanese Patent Application Sho 57-104,313, published Dec. 23, 1983; Japanese Patent Application Sho 58-127,893 published Feb. 5, 1985 (both to Lion) and U.S. patent application Ser. No. 314,627, Melanson and Sturm, filed Feb. 23, 1989. Japanese Patent Application Sho 57-080,644 (Lion), published Nov. 18, 1983, discloses the use of a broad group of hydroxypyridone compounds for dandruff control. All above cited references are incorporated herein by reference.

The combination of pyridinethione and hdyroxypyridone compounds for use in antidandruff shampoos is known in the art. Japanese Patent Application Sho 58-198, 413 (Lion), published Nov. 18, 1983, incorporated herein by reference, discloses antidandruff shampoo compositions which include a combination of zinc pyridinethione and piroctone olamine at a level from 0.05 to 5% by weight, wherein the ratio of zinc pyridinethione to piroctone olamine is from 9:1 to 1:9.

The pyridinethione/hydroxypyridone mixtures specified herein are generally used at levels of from about 0.4% to about 3% of the compositions. The weight ratio of pyridinethione salt to hydroxypyridone is generally from about 1:1 to about 5:1, preferably from about 2:1 to about 3:1, most preferred is about 2.5:1.

Selenium disulfide is a medicine used in medicated shampoos for treatment of seborrhea. U.S. Pat. No. 2,694,668, Baldwin et al., issued Nov. 16, 1954; U.S. Pat. No. 3,152,046, Kapral, issued Oct. 6, 1984; U.S. Pat. No. 4,089,945, Brinkman, issued May 16, 1978; and U.S. Pat. No. 4,885,107, Wetzel, issued Dec. 12, 1989, all incorporated herein by reference, discloses selenium disulfide as the active ingredient in antidandruff shampoo compositions.

The pyridinethione/selenium disulfide mixtures specified herein are generally used at levels of from about 1.25% to about 3% of the composition. The ratio of pyridinethione salt to selenium disulfide is generally from about 1:4 to about 2:1, preferred is about 1:1.

SYNERGIZER

When a synergizer component, defined below, is combined with the specified size platelet pyridinethion salts in a shampoo, the shampoo's antidandruff efficacy is unexpectedly enhanced. These synergizers are used at levels from about 0.5% to about 5%, preferably from about 1% to about 3% and most preferably about 2%, of the composition, and are selected from the group consisting of specific polyethylene glycols (PEG), polypropylene glycols (PPG), polyethoxy/polypropoxy copolymers (polyoxamers), polyethylenimines, polyethoxylated polyethylenimines, polyethylene oxide fatty glycerides, ethoxylated nonylphenyol, ethoxylated alcohols, polyethylene oxide carbohydrates, and mixtures thereof. Preferred synergizers herein are the polyethylene glycols containing from about 6 to about 22 ethoxy groups, particularly those having a molecular weight from about 280 to about 1000. An especially preferred synergizer is PEG-12, with a molecular weight of about 546.

PEG and PPG are known for use in shampoos as viscosity modifiers. See Goldemberg, *Advances in Cosmetic Technology*, Vol. 1 p. 70–71 (1978), incorporated herein by reference.

The PEG for use in the present invention has the formula

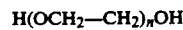

wherein n is from about 6 to about 22; preferably from about 6 to about 18. Most preferred is PEG-12 wherein n has the average value of 12, available as Carbowax 600, from Union Carbide; Polyglycol E-600, from Dow Chemical U.S.A.; and Pluracol E-600, from BASF-Wyandotte.

The PPG used in the present invention has the formula

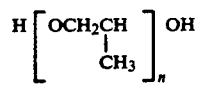

wherein n is from about 6 to about 22, preferably from about 6 to about 18. Most preferred is PPG-12wherein n has the average value of 12, available as Pluracol P-710, from BASF-Wyandotte.

Polyoxamers are polyoxyethylene/polyoxypropylene block polymers, which are useful herein as synergizers. An example of such a block polymer has the formula

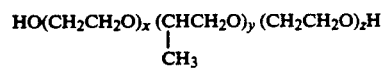

wherein the total of $x+z$ is from about 38 to about 156, and y is from about 30 to about 54. The block polymers also include polymers which have the propoxy, ethoxy, propoxy chain orientation. These synergizers are available from BASF-Wyandotte as Pluronics. Preferred for use herein is Pluronic F-68.

Other synergizers useful herein include polyethylenimines which are disclosed in U.S. Pat. No. 3,761,417, Parran, issued Sept. 25, 1973; incorporated herein by reference. These polyethyleneimines generally have the forumla

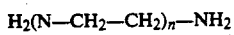

$$H_2(N-CH_2-CH_2)_n-NH_2$$

wherein n is from about 6 to about 22, preferably from about 6 to about 18. Examples of these are PEI 7 and PEI 15.

Ethoxylated polyethylenimies are also useful herein as synergizers. Such compounds are disclosed in Parran cited supra. These synergizers have the formula

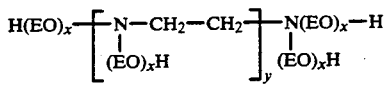

wherein y is from about 6 to about 22 and the ethoxylate groups x are independently from about 10 to about 30. An example of this is ethoxylated tetraethylene pentamine.

Ethoxylated nonylphenols are also useful herein as synergizers. These synergizers are nonionic surfactants having the formula

$$C_9H_{19}C_6H_4(OCH_2CH_2)_nOH$$

wherein n is from about 1 2to about 50. Said synergizer is also known are nonoxynol. Preferred for use herein is Nonoxynol 40.

Polyethylene oxide fatty glycerides also synergize the actives in the shampoo compositions disclosed herein. Said synergizers have the formula

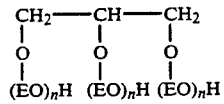

wherein EO represents —(CH$_2$—CH$_2$—O—)— and each n is independently from about 0 to about 9 with no fewer than one ethoxy group in the compound. Such ethoxylated glycerides are available from ICI Americas Incorporated as Arlatone G or PEG-40 Sorbitan Peroleate.

Polyethylene oxide carbohydrates may also be used to synergize the actives herein. Said synergizers have the formula

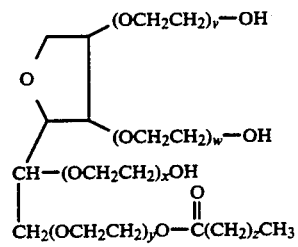

wherein the total v+w+x+y is from about 4 to about 20 and z is from about 10 to about 18. Said compounds, which are known for use in hair care products as co-surfactants and suspending agents, include the polysorbates available from ICI Americas as Tween. Preferred is Tween-20.

Lastly, ethoxylated straight chain alcohols synergize the antidandruff actives disclosed herein. Said synergizers have the formula

$$R(OCH_2CH_2)_nOH$$

wherein R represents a blend of cetyl and stearyl radicals n is from about 20 to about 55. These compounds are available from BASF Wyandotte as Plurafacs. Preferred is Plurafac A-39.

SUSPENDING AGENTS

The compositions of the present invention contain a suspending agent. Examples of suitable suspending agents include xanthan gum, long chain ($C_{16}$–$C_{22}$) acyl derivatives, long chain ($C_{16}$–$C_{22}$) amine oxides, and mixtures thereof, as are disclosed by U.S. Pat. No. 4,704,272, Oh et al., issued Nov. 3, 1987, incorporated herein by reference.

The preferred suspending agents are the ethylene glycol esters as disclosed in U.S. Pat. No. 4,885,107, Wetzel, issued Dec. 5, 1989; incorporated herein by reference. Most preferred are the diesters comprising a mixture of palmitate and stearate. The amount of stearate should be in the range of about 10% to about 42% or in the range of about 55% to about 80% with palmitate accounting for the remainder. The amount of stearate is preferably from about 60% to about 75%.

The amount of the ethylene glycol diester useful in the present invention is from about 0.5% to about 6%, preferably from about 1% to about 4%.

Water

Water is the last essential component of the present invention and forms the remainder of the composition. It is generally present at a level of from about 20% to about 90%, preferably from about 60% to about 85%, of the final composition.

OPTIONAL COMPONENTS

The shampoos herein can contain a variety of nonessential optional components suitable for rendering such composition more cosmetically, aesthetically, or functionally acceptable. Such conventional optional ingredients. well known to those skilled in the art, include preservatives, such as benzyl alcohol, methyl paraben, propyl paraben and imidazolidinyl area; cationic surfactants, such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; pH adjusting agents, such as citric acid, succinic acid, phosphoric acid, sodium hydroxide, and sodium carbonate; perfumes; and dyes. Such optional ingredients generally are used individually at a level of from about 0.01% to about 10%, preferably from about 0.5% to about 5%, by weight of the composition.

The amides may be used in lotion form shampoo compositions. Amides for use herein include alkanolamides of fatty acids known for use in shampoos as emulsifiers. Said amide enhance lathering and are generally mono- and diethanolamide of fatty acids having from about 8 to about 14 carbon atoms. Preferred are coconut monoethanolamide, coconut diethanolamide, and mixtures thereof. Other amides are those having multiple ethoxy groups such as PEG-3 lauramide.

When used, the amide is present at a level of from about 1% to about 7%, preferably from about 2% to about 5%, of the shampoo composition.

Silicone compounds may be incorporated into the shampoo compositions to impart conditioning benefits to the hair. Such silicone compounds are disclosed in U.S. Pat. No. 2,826,551, Geen, issued Mar. 11, 1958; U.S. Pat. No. 3,964,500, Drakoff, issued June 22, 1976; U.S. Pat. No. 4,152,416, Spitzer, issued May 1, 1979; U.S. Pat. No. 4,364,837, Pader, issued Dec. 21, 1982; U.S. Pat. No. 4,221,688, Johnson et al., issued Sept. 9, 1980; U.S. Pat. No. 4,515,784, Bogardus et al., issued May, 7, 1985; U.S. Pat. No. 4,704,272, Oh et al., issued Nov. 3, 1987; U.S. Pat. No. 4,728,457, Fieler et al., issued Mar. 1, 1988; U.S. Pat. No. 4,741,855, Grote et al., issued May 3, 1988; U.S. Pat. No. 4,764,363, Bolich, issued Aug. 16, 1988; U.S. Pat. No. 4,788,006, Bolich et al., issued Nov. 29, 1988; U.S. Pat. NO. 4,834,968, Bolich, issued May 30, 1989; and U.S. Pat. No. 4,842,850, Vu, issued June 27, 1989; all incorporated herein by reference.

Non-volatile silicone containing compounds are preferred herein and are used at levels of from about 0.1% to about 10%, preferably from about 0.25% to about 3%, by weight of the composition. Non-volatile silicones are selected from the group consisting of polyalkyl siloxanes, polyaryl aryl siloxanes, polyether siloxane copolymers and mixtures thereof.

Polyalkyl siloxanes useful herein include, for example, polydimethyl siloxanes (PDMS) with viscosities ranging from about 5 to 15,000,000 centipoise (cp) at 25° C. These siloxanes are available, for example, from the General Electric Company as the Viscasil series and from Dow Corning as the Dow Corning 200 series. The viscosity can be measured by means of a glass capillary viscometer as set forth in Dow Corning Corporate Test Method CTM0004, July 20, 1970.

Polyalkylaryl siloxanes that may be used include polymethylphenyl siloxanes having viscosities of from about 5 to about 15,000,000 cp at 25° C. These siloxanes are available, for example, from the General Electric Company as SF 1075 methyl phenyl fluid or from Dow Corning as 556 Cosmetic Grade Fluid.

Polyether siloxane copolymers that may be used include polypropylene oxide modified polydimethylsiloxanes. These are available, for example, from Dow Corning as CD-1248. Ethylene oxide or mixtures of ethylene oxide and propylene oxide may also be used. The water insoluble ones are preferred.

Generally, these silicone compounds described above condition the hair. The conditioning benefit is due to the ability of the siloxanes to lubricate the hair providing wet and dry combing benefits. Viscous, higher molecular weight siloxanes provide the best conditioning benefits and are therefore preferred for use in the present shampoo composition. It has been found that gums of the above described siloxane polymers are most desirable for use herein. These siloxane polymer gums are rigid as opposed to a liquid of fluid, with high mass molecular weights of from about 200,000 to about 1,000,000 and viscosities from about 100,000 cp to about 150,000,000 cp at 25° C. Such gums are discussed in detail in W. Noll, *Chemistry and Technology of Silicones*, New York Academic Press, 1968; and General Electric, Silicones and Rubber Product Data Sheet SE30, SE33, SE54 and SE76; and Mark, Bikales, Overberger, Mengle, *Encyclopedia of Science and Engineering*, Vol. 15 (2d ed., 1989), all incorporated herein by reference.

In the present invention the polydimethyl siloxane gums are preferred. These gums have a viscosity of from about 100,000 cp to about 150,000,000 cp at 25° C. The gums selected for use herein have a viscosity such that when blended with a PDMS fluid the viscosity of the blend of gum and fluid falls within this range. Such PDMS fluids used for the blending of the gum are those disclosed in U.S. Pat. No. 4,834,968, Bolich, issued May 30, 1989; incorporated herein by reference. Such PDMS fluids are used at levels from about 50% to about 60% of the total weight of said gum-fluid blend. Most preferred for the present invention is a blend containing from about 40% to about 60% PDMS fluid/from about 60% to about 40% PDMS gum. The preferred PDMS fluid is dimethicone fluid which has a viscosity of about 350 cp at 25° C. Most preferred PDMS gums are those available from The General Electric Company.

Viscosity modifiers may be added to the shampoo compositions disclosed herein. Shampoos with viscosities from about 2,000 cp to about 12,000 cp at 25° C. generally in the form of lotions offer the best cosmetic and aesthetic advantages to users. In the present invention, hydrotropes may be used as viscosity modifiers. These are selected from the group consisting of aryl sulfonates, such as ammonium xylene sulfonate; alcohols, such as polyvinyl alcohol, and ethyl alcohol; salts, such as sodium chloride, and ammonium chloride; and mixtures thereof, Some of the synergizers, such as polyethylene glycol, polypropylene glycol, polyethoxy-/polypropoxy copolymers and polyethylenimines may also have viscosity modifying effects; in some circumstances the above described viscosity modifiers may additionally be included at from about 1% to about 5% of the shampoo, to bring the viscosity of the final compositions within the range disclosed above.

METHOD OF MANUFACTURE

The antidandruff shampoo compositions disclosed herein may be made by various processes generally known in the art. All of these processes require making a number of premixes which are eventually combined with a main mix.

The surfactants preferred for use, ammonium lauryl sulfate (ALS) and ammonium laureth sulfate (AE$_3$S), are premixed. The ALS mixture contains about 25% ALS, about 0.3% preservative and the rest water. The AE$_3$S mixture is about 28% AE$_3$S, 0.3% preservative, about 4% viscosity modifier and the rest water. Some synergizers may modify the viscosity. When these synergizers are used, they should be added to the AE$_3$S premix at a level necessary to achieve desired viscosity. The remainder of the synergizer required to enhance the antidandruff activity is added with those actives. The surfactant premixes, as well as the fatty alcohols, the amide and suspending agents, are mixed together to form the main mix. Various other premixed ingredients are added to this main mix at various processing points, as described below.

The ZPT active is added to the main mix as a slurry. Additional antidandruff actives, (e.g., selenium disulfide, piroctone olamine or mixtures thereof) may be added along with the ZPT slurry.

If a silicone gum/fluid blend is to be used, it is made as a premix together with other shampoo ingredients to facilitate the uniform dispersion of said blend in the main mix.

METHOD OF USE

The present compositions are used in a conventional manner for cleaning hair. From about 0.1 g to about 20 g of the composition is applied to hair that has been wetted, generally with water, washed through the hair and rinsed out. Said method of use is repeated until the hair is clean.

EXAMPLES

The following examples illustrate the compositions of the present invention.

| Component | I | II | III | IV | V | VI |
|---|---|---|---|---|---|---|
| Ammonium Laureth Sulfate | 14.94 | 14.94 | 3.15 | 14.94 | 14.94 | 3.15 |
| Ammonium Lauryl Sulfate | 3.15 | 3.15 | 14.94 | 3.15 | 3.15 | 14.94 |
| Ammonium Xylenesulfonate | — | 3.00 | 3.00 | — | 3.00 | 3.00 |
| Ethylene Glycol Distearate | 3.00 | 3.00 | 3.00 | 3.00 | 3.00 | 3.00 |
| Coconut Monoethanolamide | 2.58 | 2.58 | 2.58 | 2.58 | 2.58 | 2.58 |
| Polyethylene Glycol 12 (molecular wt. 546) | 2.00 | — | — | 2.00 | — | — |
| Polypropylene Glycol - 12 (molecular wt. 714) | — | 2.00 | — | — | — | — |
| PEG-40 Sorbitan Peroleate | — | — | 2.00 | — | — | — |
| Nonoxynol-15 | — | — | — | — | 2.00 | — |
| PEI-15 (molecular wt. 645) | — | — | — | — | — | 2.00 |
| Silicone Gum[1] | 0.5 | 0.5 | 0.4 | 0.5 | 0.5 | 0.4 |
| Dimethicone Fluid (350 cp at 25° C.) | 0.5 | 0.5 | 0.6 | 0.5 | 0.5 | 0.6 |
| 2-Zinc Pyrithione (platelets, mean particle size of 7.7μ) | 1.0 | 1.0 | 1.0 | 1.0 | 1.0 | 1.0 |
| Piroctone Olamine | — | 1.0 | — | 0.5 | 0.75 | 0.25 |
| Selenium Disulfide | — | — | 1.0 | 0.5 | 0.25 | 0.75 |
| Cetyl Alcohol | 0.42 | 0.42 | 0.6 | 0.42 | 0.42 | 0.60 |
| Stearyl Alcohol | 0.18 | 0.18 | 0.3 | 0.18 | 0.18 | 0.30 |
| Color, perfume, preservative, pH control agent and water | | | | | Q.S. to 100% | |

[1]Silicone gum available from General Electric Co. as the Viscasil Series.

The above examples are made using the procedure that follows.

Prepare a silicone pre-mix by putting about 2% of the ammonium laureth sulfate into a process tank and heating to from about 74° C. to about 80° C. Add about 0.3% of the cetyl alcohol, about 0.1% of stearyl alcohol and the silicone gum/fluid blend to the tank. Continue to mix until all solids are melted and the mixture is uniform.

In a second process tank, add ammonium lauryl sulfate and about 2% ammonium larueth sulfate. Heat, while mixing, to form about 74° C. to about 80° C. Add the rest of the cetyl alcohol and stearyl alcohol, as well as the coconut monoethanolamide, ethylene glycol distearate. preservatives, and water. Once this is thoroughly blended, add the silicone premix. Mix until uniform and cool mixture to about 42° C.

Add the remaining ammonium laureth sulfate, the ZPT slurry, other additional actives, such as selenium disulfide, piroctone olamine, and mixtures thereof, the synergizer, perfume, color and water to the main mix tank. Mix until uniform and pump into storage containers.

When hair is washed with any of the above shampoo compositions, excellent cleaning and antidandruff controls are obtained.

| Component | VII | VIII | IX | X | XI | XII |
|---|---|---|---|---|---|---|
| Ammonium Laureth Sulfate | 11.92 | 11.92 | 11.92 | 11.92 | 11.92 | 11.92 |
| Ammonium Lauryl Sulfate | 10.42 | 10.42 | 10.42 | 10.42 | 10.42 | 10.42 |
| Ethylene Glycol Distearate | 3.00 | 3.00 | 3.00 | 3.00 | 3.00 | 3.00 |
| Coconut Monoethanolamide | 3.44 | 3.44 | 3.44 | 3.44 | 3.44 | 3.44 |
| Polyethylene Glycol-12 (molecular wt. 546) | 5.00 | 3.0 | — | — | — | — |
| Polypropylene Glycol - 12 (molecular wt. 714) | — | — | 5.0 | — | — | — |
| Polyoxamer - 105 | — | — | — | 5.0 | — | — |
| Ceteareth - 12 | — | — | — | — | 5.0 | — |
| Polysorbate 20 | — | — | — | — | — | 5.0 |
| Ammonium Xylene Sulfonate | — | 2.0 | 2.0 | 2.0 | — | 2.0 |
| 2-Zinc Pyrithione (platelets, mean particle size of 7.7μ) | 1.0 | 1.0 | 1.0 | 1.0 | 1.0 | 1.0 |
| Piroctone Olamine | — | 1.0 | — | 0.5 | 0.75 | 0.25 |
| Selenium Disulfide | — | — | 1.0 | 0.5 | 0.25 | 0.75 |
| Color, perfume, preservative, pH control and water | | | | | Q.S. to 100% | |

The following procedure is used to make Examples VII to XII.

Add the ammonium lauryl sulfate to a pre-mix tank and heat to from about 65° C. to about 77° C. Add preservative, color, coconut monoethanolamide allowing the solid to melt into solution. Add ethylene glycol distearate allowing the solid to melt into solution. Add ammonium xylene sulfonate, a synergizer, or both. Add water and mix until uniform, cooling to about 29° C.

The premix is then and added to the main mix tank. Add the ZPT slurry, other additional actives, such as selenium disulfide, piroctone olamine and mixtures thereof, synergizer, ammonium laureth sulfate, and water to the main mix tank. Mix until uniform and pump into storage containers.

When the hair is washed with any of the above shampoo compositions, excellent cleaning and dandruff control are obtained.

What is claimed is:

1. An antidandruff shampoo composition in lotion form comprising:
    (a) from about 5% to about 70% of a synthetic surfactant;
    (b) from about 0.3% to about 2% of 1-hydroxy-2-pyridinethione metal salt in platelet form having a mean particle size of from about 2 microns to about 15 microns;
    (c) from about 0.5% to about 5% of a synergizer selected from the group consisting of:
        (1) polyethylene glycols having the formula

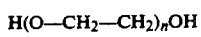
        H(O—CH$_2$—CH$_2$)$_n$OH wherein n is from about 6 to about 22;
        (2) polypropylene glycols having the formula

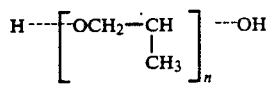

wherein n is from about 6 to about 22;
        (3) polyethoxy/polypropoxy block copolymers;
        (5) ethoxylated nonylphenols having the formula

        C$_9$H$_{19}$C$_6$H$_4$(OCH$_2$CH$_2$)$_n$OH wherein n is from about 40 to about 50;
        (6) polyethylene oxide fatty glycerides having the formula

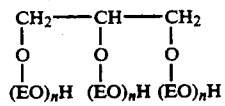

wherein (EO) represents an ethoxy group and each n is independently from about 0 to about 9, with the total number of ethoxy groups in the compound being not less than 1.
        (7) polyethylene oxide carbohydrates having the formula

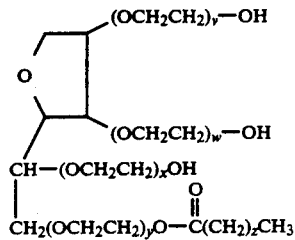

wherein the total of v+w+x+y is from about 4 to about 20, and z is from about 10 to about 18.
        (8) ethoxylated straight chain alcohols having the formula

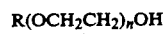
        R(OCH$_2$CH$_2$)$_n$OH wherein R represents a blend of cetyl and stearyl radicals, and n is from about 20 to about 55; and
        (9) mixture thereof;
    (d) from about 0.5% to about 6% of a suspending agent; and
    (e) the remainder water.

2. An antidandruff shampoo composition according to claim 1 wherein the synergizer is selected from the group consisting of polyethylene glycol containing from about 6 to about 22 ethoxy groups, polypropylene glycol containing from about 6 to 22 ethoxy groups, and mixtures thereof.

3. An antidandruff shampoo composition according to claim 2 additionally comprising from about 0.1% to about 10% of a nonvolatile silicone selected from the group consisting of polydimethyl siloxanes, polypropylene oxide dimethyl siloxane copolymers, and mixtures thereof, having viscosities from about 5 to about 150,000,000 centipoise at 25° C.

4. An antidandruff shampoo composition according to claim 3 additionally comprising from about 0.1% to about 1% of a second antidandruff agent selected from the group consisting of selenium disulfide, piroctone olamine, and mixtures thereof.

5. A shampoo composition according to claim 3, in lotion form, additionally comprising from about 1% to about 7% of an emulsifier selected from the group consisting of mono- and diethanolamides of fatty acids having from about 8 to about 14 carbon atoms.

6. A method of shampooing hair comprising applying to the hair that had been wet with water, from about 0.1 g to about 20 g of a composition according to claim 3, working the composition through the hair, and rinsing it from the hair.

7. An antidandruff shampoo composition according to claim 3 wherein the suspending agent is selected from the group consisting of xanthan gum, long chain (C$_{16}$-C$_{22}$) acyl derivatives, long chain (C$_{16}$-C$_{22}$) amine oxides, and mixtures thereof [at a level from about 0.5% to about 5%].

8. An antidandruff shampoo composition according to claim 7 wherein the suspending agent is an ethylene glycol C$_{16}$-C$_{22}$ diester.

9. An antidandruff shampoo composition according to claim 3 wherein the non-volatile silicone is a mixture of from about 40% to about 60% silicone gum and from about 60% to about 40% polydimethyl siloxane fluid wherein the viscosity of the mixture is from about 5 to about 200,000 centipoise at 25° C.

10. An antidandruff shampoo composition according to claim 9 wherein the silicone gum has a molecular weight between about 200,000 and about 1,000,000.

11. An antidandruff shampoo composition according to claim 10 wherein the polydimethyl siloxane has a viscosity of about 350 centipoise at 25° C.

12. An antidandruff shampoo composition according to claim 3 wherein the synthetic surfactant is selected from the group consisting of anionic surfactants, nonionic surfactants, zwitterionic surfactants, amphoteric surfactants, and mixtures thereof.

13. An antidandruff shampoo composition according to claim 12 wherein the synthetic surfactant is anionic.

14. An antidandruff shampoo composition according to claim 13 wherein the anionic surfactant is a mixture of (a) alkyl sulfate and (b) ethoxylated alkyl sulfate, having a ratio of (a) to (b) from about 5:1 to about 1:5.

15. An antidandruff shampoo composition according to claim 14 wherein the alkyl sulfate is ammonium lauryl sulfate and the ethoxylated alkyl sulfate is ammonium laureth sulfate.

16. An antidandruff shampoo composition according to claim 3 wherein the pyridinethione salt is 2-zinc pyrithione.

17. An antidandruff shampoo composition according to claim 16 wherein the 2-zinc pyrithion platelets have a mean particle size of from about 5 microns to about 9 microns.

18. An antidandruff shampoo composition according to claim 16 additionally comprising from about 1% t about 5% of a viscosity modifier selected from the group consisting of aryl sulfates, alcohols, salts, and mixtures thereof.

19. An antidandruff shampoo composition according to claim 16 wherein the synergizer is a polyethylene glycol containing from about 6 to about 18 ethylene oxide groups.

20. An antidandruff shampoo composition according to claim 19 wherein the 2-zinc pyrithione has a mean particle size of from about 5 microns to about 9 microns.

21. An antidandruff shampoo composition according to claim 20 wherein the synergizer is present at from about 1% to about 3% the composition.

22. An antidandruff shampoo composition according to claim 21 wherein the synergizer is a polyethylene glycol having the formula $H(OCH_2-CH_2)_nOH$ wherein n has an average value of 12.

23. A method of shampooing hair comprising applying to the hair that has been wet with water, from about 0.1 g to about 20 g of a composition according to claim 22, working the composition through the hair, and rinsing it from the hair.

* * * * *